(12) United States Patent
Attinger (10) Patent No.: US 11,173,241 B2
(45) Date of Patent: Nov. 16, 2021

(54) MEDICAL INSTRUMENT

(71) Applicant: Karl Storz SE & Co. KG, Tuttlingen (DE)

(72) Inventor: Jürg Attinger, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 157 days.

(21) Appl. No.: 15/974,992

(22) Filed: May 9, 2018

(65) Prior Publication Data

US 2019/0298897 A1 Oct. 3, 2019

(30) Foreign Application Priority Data

Mar. 28, 2018 (DE) .......................... 102018107439.5

(51) Int. Cl.
*A61M 1/00* (2006.01)
(52) U.S. Cl.
CPC .......... *A61M 1/7415* (2021.05); *A61M 1/774* (2021.05); *A61M 1/74* (2021.05)
(58) Field of Classification Search
CPC .............. A61M 1/0031; A61M 1/0035; A61M 1/0039; A61M 1/0041; A61M 1/0043; A61M 1/0045; A61M 3/0279; A61M 39/223; A61M 1/0064; A61M 1/774; A61M 1/74; A61M 1/0058; A61M 1/0062; A61M 1/772; A61M 2205/0216; A61B 2217/005; A61B 2217/007; A61B 2218/001; A61B 2218/002; A61B 2218/007; A61B 1/00068; A61B 1/015
See application file for complete search history.

(56) References Cited

U.S. PATENT DOCUMENTS

| | | | | |
|---|---|---|---|---|
| 3,469,582 A * | 9/1969 | Robert | ................ | A61M 1/0045 604/119 |
| 4,044,998 A * | 8/1977 | Giese | ........................ | F16K 1/34 251/331 |
| 4,504,266 A * | 3/1985 | Harle | ................... | A61M 1/0043 604/118 |
| 4,610,664 A * | 9/1986 | Harle | ................... | A61M 1/0043 251/9 |
| 4,655,197 A * | 4/1987 | Atkinson | ............ | A61M 3/0258 601/161 |
| 4,680,026 A * | 7/1987 | Weightman | ......... | A61M 1/0064 433/84 |
| 5,120,305 A * | 6/1992 | Boehringer | ......... | A61M 1/0043 604/35 |
| 5,312,332 A * | 5/1994 | Bales | ............... | A61B 17/00234 604/28 |

(Continued)

*Primary Examiner* — Shefali D Patel
*Assistant Examiner* — Avery Smale
(74) *Attorney, Agent, or Firm* — Whitmyer IP Group LLC (57) ABSTRACT

A medical instrument including a first fluid line having an end with an edge, a second fluid line, and a cavity in which the end of the first fluid line is arranged, and which is connected to the second fluid line. A wall region of the cavity is designed to be flexibly movable. In a first configuration, the flexibly movable wall region bears on the edge of the end of the first fluid line and thus closes the end of the first fluid line. In a second configuration, the flexibly movable wall region does not bear, or bears only partially, on the edge of the end of the first fluid line, such that the first fluid line and the second fluid line are fluidically connected.

17 Claims, 3 Drawing Sheets

(56) References Cited

U.S. PATENT DOCUMENTS

| | | | | |
|---|---|---|---|---|
| 5,454,784 A | * | 10/1995 | Atkinson | A61M 3/0216 |
| | | | | 604/31 |
| 5,830,214 A | * | 11/1998 | Flom | A61B 18/1482 |
| | | | | 606/41 |
| 5,967,484 A | * | 10/1999 | Morris | A61M 39/281 |
| | | | | 251/4 |
| 6,364,853 B1 | | 4/2002 | French et al. | |
| 6,918,902 B2 | | 7/2005 | French et al. | |
| 7,475,701 B2 | * | 1/2009 | Trocki | A61M 39/223 |
| | | | | 137/112 |
| 7,998,107 B2 | * | 8/2011 | Nash | A61M 1/0035 |
| | | | | 604/35 |
| 8,316,878 B2 | * | 11/2012 | Lodolo | F16K 31/385 |
| | | | | 137/315.05 |
| 2003/0047704 A1 | * | 3/2003 | Svendsen | A61M 1/0043 |
| | | | | 251/335.2 |
| 2010/0191178 A1 | * | 7/2010 | Ross | A61F 9/00736 |
| | | | | 604/22 |
| 2013/0108482 A1 | * | 5/2013 | Johnson | A61M 1/0031 |
| | | | | 417/300 |
| 2013/0303979 A1 | * | 11/2013 | Stieglitz | A61M 1/0047 |
| | | | | 604/30 |
| 2015/0182105 A1 | * | 7/2015 | Salman | A61B 1/00068 |
| | | | | 600/104 |
| 2017/0056588 A1 | * | 3/2017 | Becker | A61M 39/22 |
| 2017/0120036 A1 | * | 5/2017 | Thomas | A61M 39/24 |
| 2019/0336677 A1 | * | 11/2019 | Spaile | A61M 1/008 |

* cited by examiner

MEDICAL INSTRUMENT

CROSS-REFERENCE TO RELATED APPLICATIONS

This application claims priority to DE 102018107439.5, filed on Mar. 28, 2018.

TECHNICAL FIELD

The present invention is directed to a medical instrument with two fluid lines, the fluidic connection of which lines can be interrupted.

BACKGROUND

Some types of medical instruments, for example endoscopes, can have fluid lines. A rinsing liquid, for example, can be conveyed through a fluid line to a distal end of the endoscope and emerges at that end. Alternatively, a fluid line can allow a fluid to be aspirated out of a body cavity. Both rinsing with a rinsing fluid and aspiration of a fluid can improve visibility inside a body cavity and/or can in some other way directly or indirectly satisfy diagnostic or therapeutic purposes.

During a medical procedure, the rinsing or aspiration should generally be controllable, especially being able to be interrupted at any time and then resumed. In addition to the generally electrical control of a pump that provides the necessary overpressure or under-pressure, consideration is also given in particular to a valve, a stopcock, a slide, a shut-off flap for throttling or interrupting the stream of fluid directly at the medical instrument.

Especially in the case of medical instruments which are intended to be used just once, and whose manufacturing costs ought therefore to be particularly low, use is often made of pinch valves. However, the function of pinch valves is often very much dependent on the elasticity of the hose, and this elasticity can decrease particularly after prolonged storage. The use of a pinch valve can therefore considerably reduce the useful life, i.e. the period of time during which the medical instrument is able to be used without any limitation.

It is therefore an object of the present invention to make available an improved medical instrument, with a first fluid line whose fluidic connection to a second fluid line can be interrupted.

SUMMARY

This object is achieved by the subject matter of the independent claims.

Developments are set forth in the dependent claims.

A medical instrument comprises a first fluid line having an end with an edge, a second fluid line, and a cavity in which the end of the first fluid line is arranged, and which is connected to the second fluid line, wherein a wall region of the cavity is designed to be flexibly movable, wherein, in a first configuration, the flexibly movable wall region bears on the edge of the end of the first fluid line and thus closes the end of the first fluid line, and wherein, in a second configuration, the flexibly movable wall region does not bear, or bears only partially, on the edge of the end of the first fluid line, such that the first fluid line and the second fluid line are fluidically connected.

The medical instrument is in particular an endoscope, for example a video endoscope with an objective lens and an image sensor at the distal end of a shaft of the endoscope. In this case, either the first fluid line or the second fluid line is arranged in the shaft of the endoscope. Alternatively, the medical instrument is an endoscope with a relay lens system or with a coherent bundle of optical fibers, or with another structure by which an image generated by an objective lens at the distal end is transmitted to a proximal end of the endoscope. Alternatively, the medical instrument can be another medical instrument, e.g. a suction/irrigation handle or another instrument without an image sensor.

The fluid lines can be provided and designed, for example, in order to aspirate a fluid from an environment of a distal end of the medical instrument or to deliver a rinsing fluid to a distal end of the medical instrument. For this purpose, one of the two fluid lines in particular runs inside a shaft of the medical instrument. The other fluid line, for example, is connectable to a hose via a hose coupling and, by way of the latter, to a fluid/pressure source or an underpressure pump.

The edge of the open end of the first fluid line inside the cavity has in particular the topology of a ring. The edge can in particular be circular, elliptic, oval, square or rectangular or can have another polygonal shape, optionally with rounded corners.

The cavity in which the end of the first fluid line is arranged can have a small volume. The volume of the cavity is in particular dependent on the configuration of the flexibly movable wall region of the cavity. The cavity and its flexibly movable wall region can be designed such that, in the first configuration, the cavity only or almost only comprises the region of the end of the first fluid line. Alternatively, the cavity and its flexibly movable wall region can be designed such that, also in the first configuration of the flexibly movable wall region, the cavity completely encloses the open end of the fluid line in a ring shape or partially encloses it, i.e. encloses it in a C shape.

The cavity and its flexibly movable wall region are in particular designed such that, at least in the second configuration of the flexibly movable wall region, the cavity has a greater or much greater diameter than the lumen of the open end of the first fluid line. The diameter is measured in particular in a plane which is parallel to the edge of the end of the first fluid line.

The wall region can be completely elastically deformable or can be partially elastically and partially plastically deformable. The flexibly movable wall region can be made completely or partially from a natural rubber, a synthetic rubber or elastomer or another polymer or another organic or inorganic material. For example, the flexibly movable wall region can be formed partially or completely from a silicone rubber or a silicone elastomer.

The flexibly movable wall region can in particular be plane or substantially plane or it can be slightly curved. Alternatively, the flexibly movable wall region can have one or more folds (in particular circular or ring-like folds, i.e. closed folds, or spiral-shaped folds) similarly to a bellows.

In the first configuration, the flexibly movable wall region bears on the entire edge of the end of the first fluid line and in this way closes the open end of the first fluid line. An annular surface region of the flexibly movable wall region directed toward the end of the first fluid line, i.e. an annular surface region forming a surface of the cavity, serves as a sealing surface corresponding to the edge of the open end of the first fluid line.

In the second configuration, the flexibly movable wall region and with it this sealing surface are at least partially lifted from the edge of the open end of the first fluid line, such that the first fluid line and the second fluid line are fluidically connected via the cavity.

At a change-over between the first configuration and the second configuration, the curvature of the flexibly movable wall region is in particular changed. For example, the flexibly movable wall region is plane or substantially plane in the first configuration and is curved away from the open end of the first fluid line in the second configuration, i.e. curved concavely as seen from the direction of the cavity. Alternatively, the flexibly movable wall region in the first configuration can be curved toward the end of the first fluid line (i.e. curved convexly as seen from the direction of the cavity) and can be plane or substantially plane in the second configuration. Alternatively, the flexibly movable wall region can be curved toward the end of the first fluid line in the first configuration and can be curved away from the open end of the first fluid line in the second configuration.

At a change-over between the first configuration and the second configuration, the whole of the flexibly movable wall region can be deformed. Alternatively, only an annular region is deformed, which annular region surrounds a substantially non-deformed region.

In the case of a pinch valve, the hose is strongly deformed locally when the pinch valve is closed. This strong deformation promotes aging, in particular embrittlement, formation of cracks, and changes in elastic properties. By contrast, the flexibly movable wall region of the medical instrument described here can be designed such that, between the first configuration and the second configuration, it is only relatively slightly deformed and, in particular, is not exposed anywhere to particularly great mechanical deformation. The flexibly movable wall region can therefore be substantially more resistant to aging and can retain its elastic properties for longer. The entire medical instrument is therefore usable for a much longer period of time. Moreover, the slight deformability required of the flexible wall region means that only a slight force has to be applied in order to actuate the valve. This also permits better sealing in the closed state of the valve. The flexible properties of the valve or of the movable wall region can be adapted precisely to the desired use and do not depend on the properties of a standard medical hose kit, as is the case of a pinch valve.

A medical instrument as described here moreover comprises in particular a spring or another elastic structure which presses the flexibly movable wall region of the cavity against the edge of the end of the first fluid line.

Through the use of a spring or another elastic structure, it is possible to select and adjust a well-defined force by which the flexibly movable wall region is pressed against the edge of the end of the first fluid line. For example, when using a metal spring of suitable dimensions, this force can be maintained unchanged or substantially unchanged over a long period of time, since metal springs may only be subject to slight aging. Under these circumstances, a change in the elastic properties of the flexibly movable wall region can have only a minimal effect, if any, on the force between the flexibly movable wall region and the end of the first fluid line.

Alternatively, a spring or another elastic structure can be dispensed with if the flexibly movable wall region is designed and arranged in such a way that an elastic restoring force of the flexibly movable wall region alone generates a desired force between the flexibly movable wall region and the edge of the end of the first fluid line.

A medical instrument as described here moreover comprises in particular a structure for lifting the flexibly movable wall region of the cavity from the edge of the end of the first fluid line.

The lifting structure is in particular provided and designed to lift the flexibly movable wall region of the cavity from the edge of the end of the first fluid line counter to the elastic restoring force of the abovementioned spring or other elastic structure or of the flexibly movable wall region.

The structure is in particular provided and designed to lift the flexibly movable wall region from the edge of the end of the first fluid line in a manner that is directly manually controllable. The structure is in particular provided and designed for directly manually controllable lifting insofar as it comprises a direct mechanical coupling between a manually actuatable member and the flexibly movable wall region of the cavity. Alternatively, the lifting structure can be provided and designed to lift the flexibly movable wall region from the edge of the end of the first fluid line by means of an electromagnetic, electromotive, hydraulic, pneumatic or other drive.

In particular, a combination of a spring or of another elastic structure, which moves the flexibly movable wall region into the first configuration closing the end of the first fluid line, and of a structure for manually moving the flexibly movable wall region to the second configuration counter to the elastic restoring force of the spring or of the other elastic structure can facilitate reliable opening and closing of the end of the first fluid line and at the same time can facilitate a well-defined actuating force, which also remains unchanged after a long period of time.

A medical instrument as described here moreover comprises in particular a spring or another elastic structure which lifts the flexibly movable wall region of the cavity from the edge of the end of the first fluid line.

Alternatively, the flexibly movable wall region itself can be designed and arranged such that an elastic restoring force generated in the flexibly movable wall region itself lifts the flexibly movable wall region from the edge of the end of the first fluid line.

A medical instrument as described here moreover comprises in particular a structure for placing the flexibly movable wall region of the cavity onto the edge of the end of the first fluid line.

The placing structure is provided and designed in particular to place the flexibly movable wall region on the entire edge of the end of the first fluid line. The placing structure is provided and designed in particular to place the flexibly movable wall region of the cavity on the edge of the end of the first fluid line counter to the restoring force of a spring or of another elastic structure or counter to an elastic restoring force of the flexibly movable wall region itself.

The placing structure is in particular provided and designed to place the flexibly movable wall region of the cavity on the edge of the end of the first fluid line in a manner that is directly manually controllable. The placing structure is in particular provided and designed for directly manually controllable placement of the flexibly movable wall region onto the edge of the end of the first fluid line insofar as it comprises a direct mechanical coupling between a manually actuatable member and the flexibly movable wall region.

In particular, a combination of a spring or of another elastic structure, which moves the flexibly movable wall region into the second configuration freeing the end of the first fluid line, and of a structure for manually moving the flexibly movable wall region to the first configuration counter to the elastic restoring force of the spring or of the other elastic structure can facilitate reliable opening and closing of the end of the first fluid line and at the same time can facilitate a well-defined actuating force, which also remains unchanged after a long period of time.

A spring or another elastic structure whose restoring force moves the flexibly movable wall region into one configuration, and a structure for moving the flexibly movable wall region to the other configuration counter to the restoring force, can facilitate a positively controlled actuation of the flexibly movable wall region in both directions. The control of the fluidic connection or separation of the first fluid line and the second fluid line can thus be particularly robust and long-lasting.

In a medical instrument as described here, the structure for controllable lifting or placement of the flexibly movable wall region comprises in particular an extension piece and a force-transmitting structure, which is mechanically coupled to the extension piece.

The extension piece can be formed on a side of the flexibly movable wall region directed away from the cavity.

The extension piece is in particular designed integrally or monolithically with the flexibly movable wall region. The flexibly movable wall region is in particular produced at the same time with the extension piece, for example in the context of injection molding. Alternatively, the extension piece can, for example, be vulcanized onto the side of the flexibly movable wall region directed away from the cavity or can in some other way be cohesively bonded to the flexibly movable wall region. The extension piece is in particular cylindrical or substantially cylindrical, conical or pyramidal with a cross section (in a plane orthogonal to the direction of movement of the flexibly movable wall region) which can be circular, elliptic, oval, square or rectangular or of another polygonal shape. The force-transmitting structure comprises or in particular is a component formed from a metal wire, for example a rod.

In a medical instrument as described here, the extension piece has in particular an opening or another concave region, wherein the force-transmitting structure engages in the opening or the other concave region.

The extension piece has in particular a through-hole or another bore or another opening transverse to the intended direction of movement of the flexibly movable wall region. The force-transmitting structure has in particular a hook or a stub axle which engages in the bore or another opening.

In a medical instrument as described here, the structure for controllable lifting moreover comprises in particular a support member, which at least partially encloses the extension piece or forms the extension piece.

The support member is in particular tubular or substantially tubular with an annularly closed cross section or an almost annularly closed (C-shaped) cross section. The support member is in particular made of a material that is inflexible compared to the material of the flexibly movable wall region.

Despite both the flexibly movable wall region and the extension piece being made of the same flexible material, the support member can have the effect that no deformation or substantially no deformation takes place within the extension piece during the intended use. For this purpose, a pre-tensioning of the extension piece within the support member is in particular provided, such that the support member always bears on the side of the flexibly movable wall region directed away from the cavity. Despite the medical instrument being of a simple construction, the support member can facilitate precise controllability of the flexibly movable wall region.

If the extension piece is not integrally formed on the movable wall region, it is formed by the support member itself. The support member can then also be made solid.

The support member, like the extension piece, is in particular mechanically coupled directly to the force-transmitting structure.

In a medical instrument as described here, the spring or the other elastic structure engages in particular on the support member, wherein the force-transmitting structure moreover engages in a bore or another opening or another concave region in the support member or is in some other way mechanically coupled directly to the support member.

In particular, the support member has a bore or another opening oriented transversely with respect to the intended direction of the force to be transmitted and with respect to the movement of the flexibly movable wall region. This bore or opening can be flush with a corresponding bore or other opening in the extension piece on the flexible wall region when the extension piece is mechanically tensioned within the support member in an intended manner. In this case, the part of the force-transmitting structure that engages simultaneously in the bore or other opening of the extension piece and in the bore or other opening of the support member brings about the described mechanical pre-tensioning of the extension piece, which can facilitate precise movement of the flexibly movable wall region.

In a medical instrument as described here, the structure for controllably lifting the flexibly movable wall region comprises in particular a lever or a slide or a button or another manually actuatable member which is arranged at or near a proximal end of a grip member of the medical instrument, wherein the cavity is arranged at or near a distal end of the grip member, and wherein the force-transmitting structure mechanically couples the lever or the slide or the other manually actuatable member to the flexibly movable wall region.

The lever or the slide or the other manually actuatable member is in particular arranged within the proximal third or the proximal quarter of the length of the grip member. The cavity is in particular arranged within the distal third or the distal quarter of the length of the grip member. The distal end of the grip member is in particular rigidly connected to the proximal end of a shaft of the medical instrument.

The force-transmitting structure can at the same time facilitate an ergonomically advantageous positioning of the lever or slide or other manually actuatable member near the proximal end of the grip member, and a structurally advantageous positioning of the cavity near the distal end of the grip member.

A medical instrument as described here moreover comprises in particular a fluid line member, which has the end of the first fluid line and an end of the second fluid line. Furthermore, or optionally, it comprises a fastening member by which an annularly closed sealing surface of the flexibly movable wall region, or of a deformable member of which the flexibly movable wall region is a constituent part, is pressed against an annularly closed sealing surface of the fluid line member.

The cavity lies between the fluid line member and the flexibly movable wall region. The fluid line member is in particular formed integrally or monolithically with the end of the first fluid line and the end of the second fluid line. In particular, the fluid line member, including the end of the first fluid line and the end of the second fluid line, is produced in a single method step, for example as a single common injection molding.

On account of its material and/or its geometry (especially wall thicknesses), the fluid line member is in particular much less flexible or deformable than the flexibly movable wall region of the cavity. The materials and wall thicknesses of the fluid line member and of the flexibly movable wall region are in particular chosen such that, under the force arising during the intended use of the medical instrument (in particular those transmitted by the described force-transmitting structure), the maximum deformation of the fluid line member at any location is at most one tenth or at most one hundredth or at most one thousandth of the maximum deformability of the flexibly movable wall region.

Through its geometry (especially its wall thicknesses and cross sections), the fastening member is in particular designed such that it has much less flexibility or deformability than the flexibly movable wall region.

In a medical instrument as described here, the flexibly movable wall region is in particular a constituent part of a substantially cup-shaped deformable member. The cup-shaped deformable member can then be fitted onto the fluid line member, for example in the manner of a cap, and can in this way form the cavity. For this purpose, the portion of the fluid line near the proximal end thereof and the portion of the second fluid line near the distal end thereof can be arranged parallel or substantially parallel to each other.

The fastening member can additionally be substantially cup-shaped, wherein an annular edge region of the fastening member presses an annular sealing surface of the cup-shaped deformable member radially against an annular sealing surface of the fluid line member.

The flexibly movable wall region is in particular the bottom of the cup-shaped or substantially cup-shaped deformable member. The annular region of the fastening member, the lateral wall of the cup-shaped deformable member with its annular sealing surface, and the annular sealing surface on the fluid line member are in particular arranged concentrically in the region of the annular sealing surfaces.

In a medical instrument as described here, the cup-shaped fastening member in particular at least partially encloses the cup-shaped deformable member.

In a medical instrument as described here, the cup-shaped deformable member is in particular at least partially arranged in the cup-shaped fastening member.

In a medical instrument as described here, the fastening member has in particular an opening in which the extension piece is arranged, or through which the force-transmitting structure engages.

In a medical instrument as described here, the fastening member has in particular a tubular portion which surrounds the opening and guides the extension piece or the support member with minimal play and minimal friction.

The tubular portion has in particular an inner cross section which is adapted to the outer cross section of the extension piece or of the support member such that the extension piece or the support member is guided with form-fit engagement in the tubular portion at the fastening member. At the same time, the aforementioned spring or other elastic structure, which presses the flexibly movable wall region against the edge of the end of the first fluid line, can be supported on the tubular portion, for example on an inwardly protruding collar. In this case, the extension piece, optionally the support member, the spring or the other elastic structure and the tubular portion on the fastening member are arranged concentrically.

In a medical instrument as described here, the fluid line member and the fastening member are connected to each other in particular by means of a latch connection or by another form-fit engagement.

The flexibly movable wall region, or a deformable member that comprises the flexibly movable wall region, is in particular arranged between the fluid line member and the fastening member such that an edge region of the flexibly movable wall region or of the deformable member is held between the fluid line member and the fastening member by clamping, i.e. by frictional or force-fit engagement. With the latch connection, therefore, the fluid line member, the flexibly movable wall region, or a deformable member with the flexibly movable wall region, and the fastening member can be joined together at the same time in a single method step.

A medical instrument as described here is in particular an endoscope with a shaft, wherein the first fluid line or the second fluid line is arranged in the shaft.

The fluid line arranged in the shaft is provided and designed in particular to aspirate a fluid from an environment of the distal end of the shaft or to deliver a rinsing fluid to the distal end of the shaft.

BRIEF DESCRIPTION OF THE DRAWINGS

Embodiments are explained in more detail below with reference to the attached figures, in which.

DETAILED DESCRIPTION

Figure 1:
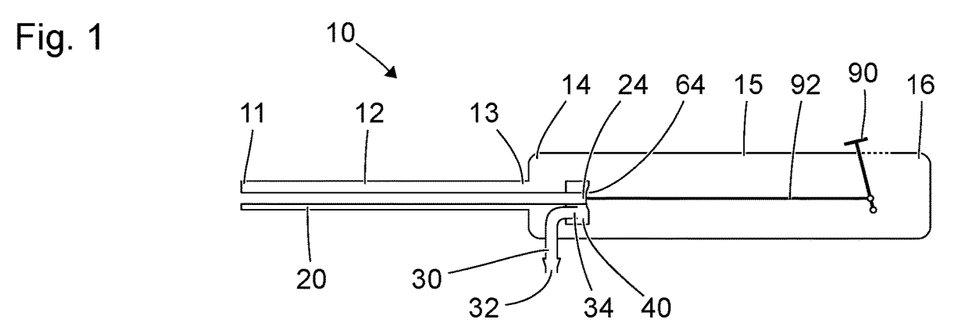
FIG. 1 shows a schematic view of a medical instrument.

FIG. 1 shows a schematic view of an endoscope 10, of which the distal end 11 is formed by the distal end of a shaft 12. As is indicated in FIG. 1, the shaft 12 be straight or curved, rigid or flexible. The proximal end 13 of the shaft 12 is connected to the distal end 14 of a grip member 15. The proximal end 16 of the grip member 15 forms the proximal end of the endoscope 10.

The endoscope 10 can have one or more structures for generating and/or transmitting illumination light to the distal end 11 and for illuminating an environment of the distal end 11 of the endoscope. These structures are not shown in FIG. 1. The endoscope 10 can moreover have one or more objective lenses at the distal end 11 for generating one or more images of the environment of the distal end 11 of the endoscope, and one or more image sensors for capturing the one or more images, and/or one or more coherent bundles of optical fibers, or one or more relay lens systems or other structures for transferring the image or the images to the grip member 15, which structures are not shown in FIG. 1.

The endoscope 10 moreover has a first fluid line 20, which is arranged in the shaft 12 of the endoscope 10 and extends from the distal end 11 of the endoscope 10 into the grip member 15. The endoscope 10 moreover has a second fluid line 30, which has an end 32 located outside the grip member 15 and indicated in FIG. 1 as a spout.

A proximal end 24 of the first fluid line 20 and a further end 34 of the second fluid line 30 are arranged inside a cavity 40 in the grip member 15. The cavity 40 is closed, in particular hermetically closed, apart from the two accesses via the first fluid line 20 and the second fluid line 30. Fluids can thus enter the cavity 40 or leave the cavity 40 only through the first fluid line 20 or the second fluid line 30.

The cavity 40 has a flexibly movable wall region 64. A manually actuatable lever 90 near the proximal end 16 of the grip member 15 is mechanically coupled to the flexibly movable wall region 64 via a coupling rod 92 as force-transmitting structure. A movement of the lever 90 therefore causes a movement of the flexibly movable wall region 64 of the cavity 40.

FIG. 1 shows a situation or configuration in which the lever 90 adopts a distal position and the flexibly movable wall region 64 of the cavity 40 is curved inward into the cavity 40. In the situation shown in FIG. 1, the flexibly movable wall region 64 bears on the proximal end 24 of the first fluid line 20 and closes same. A fluid in the first fluid line 20 cannot pass into the cavity 40 and the second fluid line 30. A fluid in the second fluid line 30 and in the cavity 40 cannot pass into the first fluid line. The first fluid line 20 and the second fluid line 30 are separate from each other.

Figure 2:
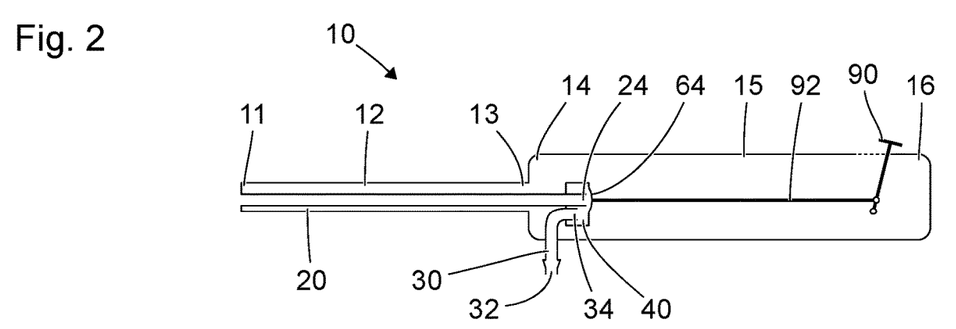
FIG. 2 shows a further schematic view of the medical instrument from FIG. 1.

FIG. 2 shows a further schematic view of the endoscope 10 shown in FIG. 1. The nature of the view in FIG. 2 corresponds to that of FIG. 1.

FIG. 2 shows a situation or configuration in which the manually actuatable lever 90 adopts a proximal position and the flexibly movable wall region 64 of the cavity 40 is curved away from the cavity 40 and from the proximal end 24 of the first fluid line 20. In the configuration shown in FIG. 2, the flexibly movable wall region 64 does not close the proximal end 24 of the first fluid line 20. A fluid can flow from the first fluid line 20 into the cavity 40 and from there onward into the second fluid line 30, or vice versa.

For an aspiration function, the end 32 of the second fluid line 30 arranged outside the grip member 15 can, for example, be connected by means of a hose to a suction pump or to another underpressure source. In the configuration shown in FIG. 2, the underpressure generated by the underpressure source spreads through the second fluid line 30, the cavity 40 and the first fluid line 20 as far as the distal end 11 of the endoscope 10 and can permit aspiration of a fluid from an environment of the distal end 11 of the endoscope 10. Small solids can also be aspirated with the fluid.

For a rinsing function, the end 32 of the second fluid line 30 arranged outside the grip member 15 of the endoscope 10 can, for example, be connected by means of a hose to a pressure and fluid source. This pressure and fluid source comprises, for example, a fluid reservoir and a pump, or a fluid reservoir arranged higher up than the endoscope 10. In the configuration shown in FIG. 2, a rinsing fluid, for example, can flow through the second fluid line 30, the cavity 40 and the first fluid line 20 to the distal end 11 of the endoscope 10 and emerge there.

In the configuration shown in FIG. 1, the aspiration function or rinsing function is interrupted by the closure of the proximal end 24 of the first fluid line 20 by means of the flexibly movable wall region 64.

Figure 3:
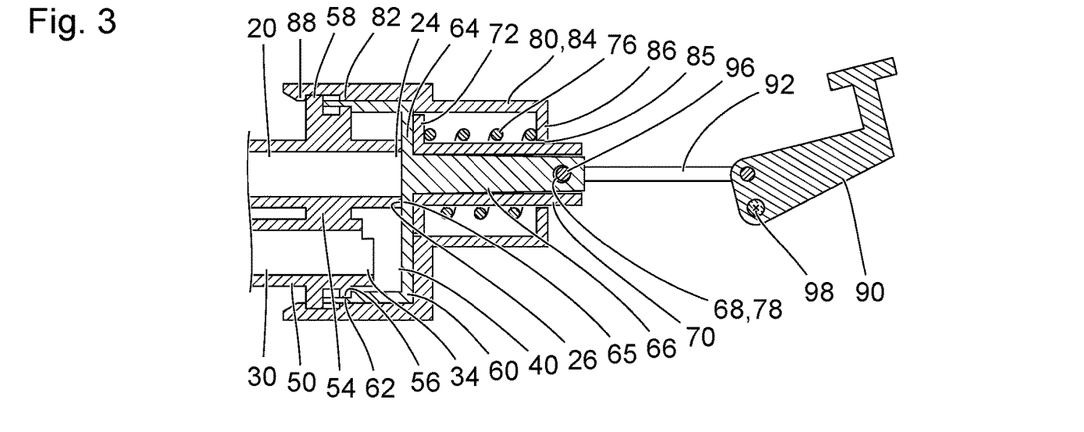
FIG. 3 shows a schematic and enlarged sectional view of parts of the medical instrument from FIGS. 1 and 2.

FIG. 3 shows a schematic and enlarged sectional view of an embodiment of members forming or enclosing the cavity 40, of the lever 90, and of the coupling rod 92. The section plane of FIG. 3 is in particular parallel to the drawing planes of FIGS. 1 and 2 and contains longitudinal axes of the fluid lines 20, 30, at the ends 24, 34 thereof arranged in or at the cavity 40.

The cavity 40 is enclosed by a fluid line member 50 and a deformable member 60.

The fluid line member 50 comprises the proximal end 24 of the first fluid line and the end 34 of the second fluid line. In the example shown, the fluid line member 50, including the proximal end 24 of the first fluid line 20 and the end 34 of the second fluid line 30, is of a monolithic design, for example in the form of a plastic member produced in a common method step. The fluid line member 50 can additionally monolithically comprise the entire second fluid line 30 and/or the entire first fluid line 20. Alternatively, the fluid line member can be assembled from several members. The fluid line member 50 is in particular produced from a plastic of low elasticity and/or has wall thicknesses and cross sections that make the fluid line member 50 stiff, i.e. not very deformable.

The fluid line member 50 comprises in particular a wall region 54 which extends orthogonally with respect to the section plane of FIG. 3. The wall region 54 is in particular circular or substantially circular or elliptic or substantially elliptic. The first fluid line 20 and the second fluid line 30 each penetrate the wall region 54. In the example shown, the portion of the first fluid line 20 near its proximal end 24 and the portion of the second fluid line 30 near its end are arranged parallel or substantially parallel to each other and orthogonally or substantially orthogonally with respect to the wall region 54.

The deformable member 60 is substantially cup-shaped. The edge of the cup-shaped deformable member 60 bears on the edge of the wall region 54. In particular, an annular sealing surface 62 near the edge of the cup-shaped deformable member 60 bears on an annular sealing surface 56 at the edge of the wall region 54 of the fluid line member 50.

The bottom of the cup-shaped deformable member 60 forms the flexibly movable wall region 64 already described with reference to FIGS. 1 and 2. The surface region of the flexibly movable wall region 64 directed toward the cavity 40 forms a sealing surface 65 which, in the configuration shown in FIG. 3, bears on the edge 26 of the proximal end 24 of the first fluid line 20.

On its side directed away from the cavity 40, the substantially cup-shaped deformable member 60 has an extension piece 66. In the example shown in FIG. 3, the extension piece 66 is cylindrical or slightly conical with a cross section that slightly decreases as the distance from the flexibly movable wall region 64 increases. The extension piece 66 is arranged opposite the proximal end 24 of the first fluid line 20. In the example shown in FIG. 3, the cross section of the extension piece 66 is only slightly smaller than the cross section of the proximal end 24 of the first fluid line 20. At the end of the extension piece 66 directed away from the flexibly movable wall region 64, an opening 68 is provided in the form of a through-hole.

The deformable member 60 is made from an elastic material and, especially in the flexibly movable wall region 64, has a wall thickness that permits a deformation of the flexibly movable wall region 64.

The extension piece 66 is surrounded by a tubular or substantially tubular support member 70. The support member 70 extends substantially along the entire length of the extension piece 66. At its edge directed toward the flexibly movable wall region 64, the support member 70 has an outwardly protruding collar 72. At its end directed away from the outwardly protruding collar 72, the support member 70 has an opening 78 in the form of a through-hole, which is arranged substantially flush with the opening 68 in the extension piece 66 of the deformable member 60.

In the configuration shown in FIG. 3, the outwardly protruding collar 72, in a surface annularly enclosing the extension piece 66, bears on the flexibly movable wall region 64. An end of a helical spring 76 presses against the outwardly protruding collar 72 of the support member 70 and thus presses the outwardly protruding collar 72 against the flexibly movable wall region 64 and presses the flexibly movable wall region 64 against the edge 26 of the proximal end 24 of the first fluid line 20.

A fastening member 80 substantially encloses the deformable member 60 and the support member 70. In the environment of the cavity 40, the fastening member 80 is substantially cup-shaped and partially bears flat on the outer face of the deformable member 60 directed away from the cavity 40. An edge of the cup-shaped region of the fastening member 80 forms an annular pressing region 82, which exerts radial pressure on an edge region of the deformable member 60 and presses the annular sealing surface 62 of the deformable member 60 against the annular sealing surface 56 at the edge of the wall region 54 of the fluid line member 50.

The fastening member 80 has a tubular extension piece 84, which substantially encloses the extension piece 66 on the deformable member 60 and the support member 70 and completely encloses the spring 76. At an end directed away from the cavity 40, the tubular extension piece 84 of the fastening member 80 has an opening 85, which is delimited or enclosed by an inwardly protruding collar 86 on the tubular extension piece 84. The end of the extension piece 66 of the deformable member 60 directed away from the cavity 40 and the end of the support member 70 directed away from the cavity 40 protrude through the opening 85, such that the opening 68 in the extension piece 66 and the opening 78 in the support member 70 are arranged outside the fastening member 80. The end of the spring 76 directed away from the cavity 40 is supported on the inner face of the inwardly protruding collar 86 on the tubular attachment piece 84.

In order to take up the force of the spring 76 or, to put it another way, in order to prevent a movement of the fastening member 80 away from the fluid line member 50 (to the right in FIG. 3) despite the mechanical tensioning of the spring 76, corresponding latching lugs 58, 88 are provided on the fluid line member 50 and on the fastening member 80. The latching lugs 58, 88 on the fluid line member 50 and on the fastening member 80 engage behind each other and thus create a form-fit connection of the fastening member 80 to the fluid line member 50. In the example shown in FIG. 3, the latching lugs 58 on the fluid line member 50 are arranged at the outer circumference of the wall region 54 of the fluid line member 50.

In the embodiment shown in FIG. 3, in contrast to what is indicated FIGS. 1 and 2, the lever 90 is substantially L-shaped or Z-shaped. The lever 90 is pivotable about a pivot axis 98 orthogonal to the section plane of FIG. 3.

The coupling rod 92 is formed by a piece of metal wire, for example, both ends of which are each bent 90 degrees into an L shape. The end 96 of the coupling rod 92 directed toward the cavity 40 is arranged in the opening 68 in the extension piece 66 of the deformable member 60 and in the opening 78 in the support member 70. The other end of the coupling rod 92 is arranged in a corresponding opening in the lever 90.

The coupling rod 92 couples the lever 90 and the flexibly movable wall region 64 in such a way that a pivoting movement of the lever 90 about its pivot axis 98 causes a deformation and movement of the flexibly movable wall region 64.

Without an external, in particular manually generated force on the lever 90, the elastic restoring force of the spring 76 presses the support member 70 and the flexibly movable wall region 64 against the edge 26 of the proximal end 24 of the first fluid line. The flexibly movable wall region 64 closes the proximal end 24 of the first fluid line 20. In this way, the first fluid line 20 is separated from the second fluid line 30. Passage of a fluid from the first fluid line 20 through the cavity 40 into the second fluid line 30 is not possible, nor is passage of a fluid from the second fluid line 30 through the cavity 40 into the first fluid line 20.

Figure 4:
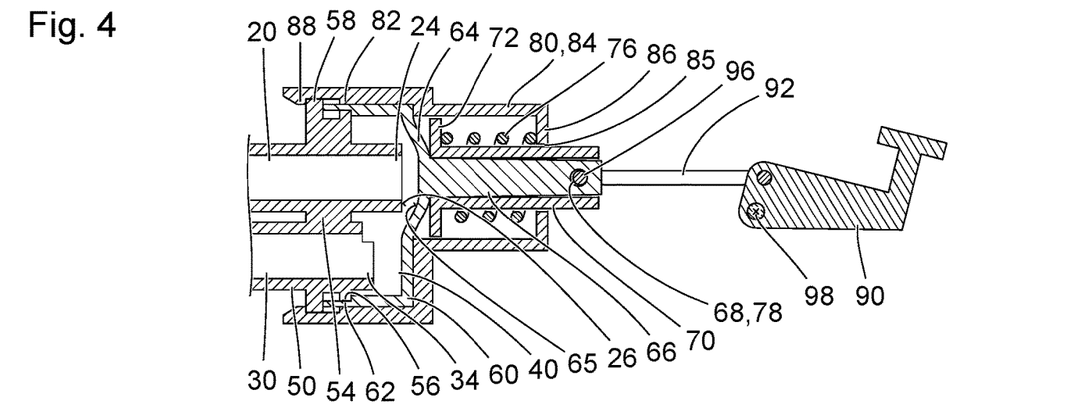
FIG. 4 shows a further schematic and enlarged sectional view of parts of the medical instrument from FIGS. 1 to 3.

FIG. 4 shows a further schematic sectional view of the members described with reference to FIG. 3, here in a further situation or configuration. The nature of view in FIG. 4 corresponds to that of FIG. 3. Whereas the configuration shown in FIG. 3 corresponds to or resembles the configuration shown in FIG. 1, the configuration shown in FIG. 4 corresponds to or resembles the configuration shown in FIG. 2.

Proceeding from the configuration shown in FIG. 3, the lever 90 can be pivoted about is pivot axis 98 to the position shown in FIG. 4, by means of an external force, in particular a manually generated force. The mechanical coupling of the lever 90 to the flexibly movable wall region 64, provided by the coupling rod 92, the extension piece 66 on the deformable member 60, and the support member 70, has the effect that, in the position of the lever 90 shown in FIG. 4, the flexibly movable wall region 64 is deformed and moved away from the edge 26 of the proximal end 24 of the first fluid line 20. The change from the configuration shown in FIG. 3 to the configuration shown in FIG. 4 takes place counter to the elastic restoring force of the spring 76. As soon as there is no longer any force acting externally on the lever 90, the system returns to the configuration shown in FIG. 3.

In the configuration shown in FIG. 4, the flexibly movable wall region 64 does not close the proximal end 24 of the first fluid line 20. The first fluid line 20 and the second fluid line 30 are fluidically connected via the cavity 40. The passage of a fluid from the first fluid line 20 through the cavity 40 into the second fluid line 30 is possible, as also is the passage of a fluid from the second fluid line 30 through the cavity 40 into the first fluid line 20.

In the configuration shown in FIG. 4, the annular shape of the cavity 40 and the position of the end 34 of the second fluid line 34 far apart from the flexibly movable wall region 64 facilitate the passage of a fluid between the fluid lines 20, 30. Since the end 34 of the second fluid line 30 is spaced far apart from the flexibly movable wall region 64, there is only a slight flow resistance to the passage of a fluid from the second fluid line 30 into the cavity 40 and vice versa. The annular shape of the cavity 40 means that, in the situation shown in FIG. 4, a fluid can flow about the entire circumference of the edge 26 of the proximal end 24 of the first fluid line 20, past this edge 26, from the first fluid line 20 into the cavity 40 or vice versa.

Figure 5:
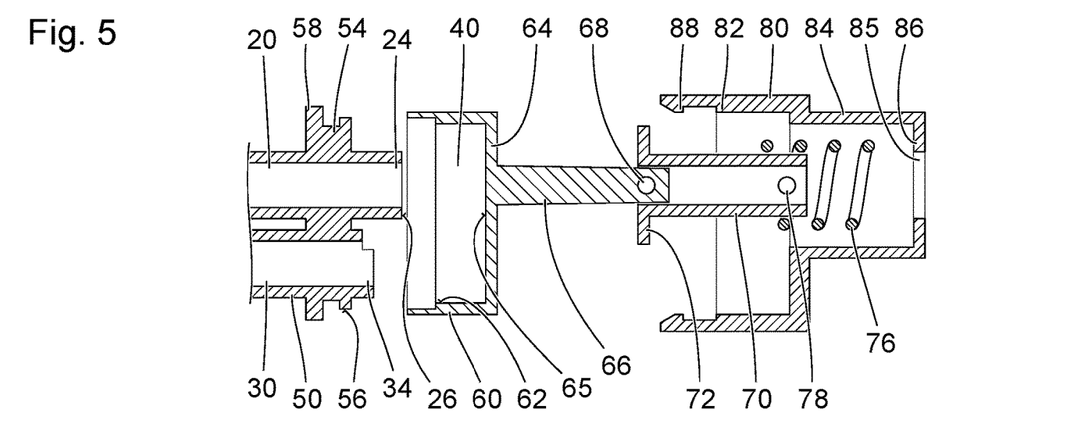
FIG. 5 shows a further schematic and enlarged sectional view of parts of the medical instrument from FIGS. 1 to 4.

FIG. 5 shows a further schematic sectional view of members that have been described with reference to FIGS. 3 and 4. The section plane of FIG. 5 corresponds to the section planes of FIGS. 3 and 4. In FIG. 5, the fluid line member 50, the deformable member 60, the support member 70, the helical spring 76 and the fastening member 80 are shown spaced apart from one another, as in an exploded view. All of the members 50, 60, 70, 76, 80 are shown staggered relative to each other in one direction (a horizontal direction in the view in FIG. 5). All of the members 50, 60, 70, 76, 80 can be moved toward one another in this direction in order to be assembled and, in the configuration shown in FIGS. 3 and 4, connected to one another with form-fit engagement by the latching lugs 58, 88.

Certain features of the members 50, 60, 70, 80 can be seen more clearly in FIG. 5. These include the radially outwardly oriented annular sealing surface 56 on the outer circumference of the wall region 54 of the fluid line member 50, and the corresponding, radially inwardly oriented annular sealing surface 62 near the edge of the here substantially cup-shaped deformable member 60. Since they are illustrated spaced apart from one another, FIG. 5 also clearly shows the edge 26, functioning as sealing surface, of the proximal end 24 of the first fluid line 20, and the corresponding sealing surface 65 on the flexibly movable wall region 64, which sealing surface 65 is formed by an annular subregion, opposite the edge 26 of the proximal end 24 of the first fluid line 20, on the surface of the flexibly movable wall region 64 directed toward the cavity 40.

FIG. 5 also shows the opening 78 at the end of the support member 70 directed away from the outwardly protruding collar 72. The here tubular support member 70 has in particular two openings 78 lying opposite each other, of which one lies in front of the section plane of FIG. 5 and is therefore not visible, but it is flush with the opening 78 that can be seen in FIG. 5.

In the assembled configuration shown in FIGS. 3 and 4, the opening 68 in the extension piece 66 of the deformable member 60 and the openings 78 in the support member 70 are flush. In the state when the deformable member 60 is free of tension or is minimally tensioned, i.e. in particular before assembly with the support member 70 and the coupling rod 92, the distance of the opening 68 in the extension piece 60 from the flexibly movable wall region 64 is in particular slightly smaller than the distance of the openings 78 in the support member 70 from the end of the support member 70 to be directed toward the flexibly movable wall region 64. Therefore, after the distal end 96 of the coupling rod 92 has been inserted into the openings 78 in the support member 70 and into the opening 68 in the extension piece 66, the extension piece 66 and the support member 70 are mechanically tensioned relative to each other. This mechanical tensioning is in particular chosen such that, during the intended use, the surface of the flexibly movable wall region 64 directed away from the cavity 40 always bears (as indicated in FIG. 4) on the end of the support member 70 directed toward the cavity 40, at least near the transition to the extension piece 66. Since the support member 70 has a slight deformability on account of the elastic properties of its material and/or its wall thicknesses and cross sections, this mechanical tensioning of the extension piece 66 with respect to the support member 70 reduces the elastic play in the mechanical coupling between the lever 90 (cf. FIGS. 3 and 4) and the flexibly movable wall region 64.

The protrusion of the latching lugs 88 with respect to the annular pressing region 82 can also be clearly seen in FIG. 5.

Figure 6:
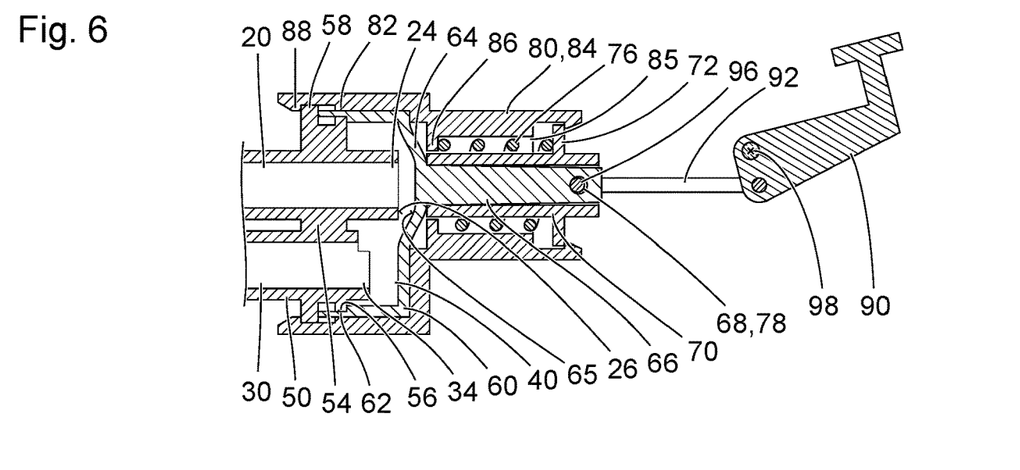
FIG. 6 shows a schematic and enlarged sectional view of an alternative embodiment of parts of the medical instrument from FIGS. 1 and 2.

FIG. 6 shows a schematic sectional view of members 50, 60, 70, 76, 80, 90, 92 of a further embodiment of the endoscope shown in FIGS. 1 and 2.

In terms of certain features, properties and functions, the embodiment shown in FIG. 6 is similar to the embodiment shown in FIGS. 3 to 5. Features, properties and functions that distinguish the members shown in FIG. 6 from the members shown in FIGS. 3 to 5 are in particular described below.

The fluid line member 50 and the deformable member 60, and therefore also the cavity 40, correspond to the members described with reference to FIGS. 3 to 5. The support member 70 and the fastening member 80 differ from those shown in FIGS. 3 to 5, specifically in that the positions of the outwardly protruding collar 72 on the support member 70 and of the inwardly protruding collar 86 on the fastening member 80 are changed around. The outwardly protruding collar 72 on the support member 70 bears on the end of the spring 76 directed away from the cavity 40, and the inwardly protruding collar 86 on the fastening member 80 bears on the end of the spring 76 directed toward the cavity 40. The elastic restoring force of the spring 76 moves the support member 70 and the extension piece 66 on the deformable member 60, and therefore also the flexibly movable wall region 64, into the positions shown in FIG. 6 when no external force is being exerted on the lever 90 Therefore, the first fluid line 20 and the second fluid line 30 are fluidically connected to each other when the lever 90 is not actuated.

By pivoting of the lever 90, in particular manually, to the position shown in FIG. 4, the coupling rod 92, the support member 70, the extension piece 66, and therefore also the flexibly movable wall region 64 of the deformable member 60, can be moved toward the proximal end 24 of the first fluid line 20 until the sealing surface 65 on the flexibly movable wall region 64 bears on the edge 26 of the proximal end 24 of the first fluid line 20, closes the proximal end 24 of the first fluid line 20 and thus separates the first fluid line 20 from the second fluid line 30.

Figure 7:
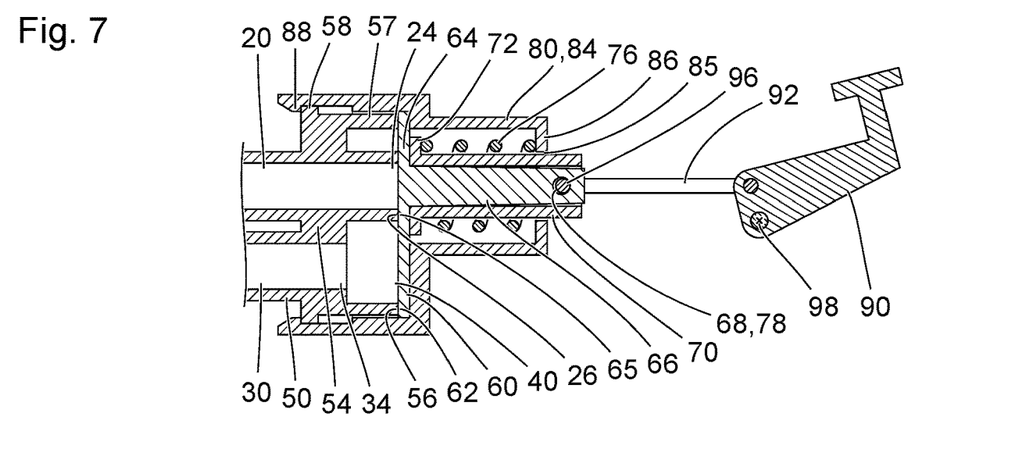
FIG. 7 shows a schematic and enlarged sectional view of a further alternative embodiment of parts of the medical instrument from FIGS. 1 and 2.

FIG. 7 shows a schematic sectional view of members 50, 60, 70, 76, 90, 92 of a further embodiment of the endoscope shown in FIGS. 1 and 2. In terms of certain features, properties and functions, the members 50, 60, 70, 76, 90, 92 shown in FIG. 7 are similar to or correspond to the members shown in FIGS. 3 to 6. Features, properties and functions that distinguish the members shown in FIG. 7 from the members shown in FIGS. 3 to 6 are in particular described below.

The fluid line member 50 shown in FIG. 7 differs from the fluid line members described with reference to FIGS. 3 to 6 in that the end 34 of the second fluid line 30 directed toward the cavity 40 does not protrude into the cavity 40, but terminates flush with the wall region 54 of the fluid line member 50. This is also possible in the fluid line members shown in FIGS. 3 to 6. Conversely, in the fluid line member 50 shown in FIG. 7, it is also possible, as in the fluid line members shown in FIGS. 3 to 6, that the end 34 of the second fluid line 30 directed toward the cavity 40 protrudes into the cavity 40.

The fluid line member 50 shown in FIG. 7 moreover differs from the fluid line members described with reference to FIGS. 3 to 6 in that a cylindrical wall region 57 is provided on the outer edge of the substantially plane wall region 54 and laterally encloses the annular cavity 40. The fluid line member 50 is thus formed in a cup shape in the environment of the cavity 40.

The deformable member 60 shown in FIG. 7 differs from the deformable members shown in FIGS. 3 to 6 in that it is not cup-shaped, and instead it has only the flexibly movable wall region 64 in the environment of the cavity 40. An annular sealing surface 62 on the deformable member 60, namely at or near the outer edge of the flexibly movable wall region 64, is pressed by the fastening member 80, in a direction parallel to the intended direction of movement of the flexibly movable wall region 64 (horizontally in FIG. 7), against a corresponding annular sealing surface 56 at the edge of the cylindrical wall region 57 of the fluid line member 50.

The support member 70 and the fastening member 80 are moreover identical or similar to those shown in FIGS. 3 to 5. When the lever 90 is not actuated, the flexibly movable wall region 64 closes the proximal end 24 of the first fluid line 20 and thus separates the first fluid line 20 from the second fluid line 30. By actuating the lever 90 counter to the elastic restoring force of the spring 76, the flexibly movable wall region 64 can be lifted from the edge 26 of the proximal end 24 of the first fluid line (similarly to what is shown in FIG. 4), in order to fluidically connect the first fluid line 20 and the second fluid line 30 and permit passage of a fluid between the first fluid line 20 and the second fluid line 30.

Alternatively, and in contrast to the view in FIG. 7, the support member 70 and the fastening member 80 can be designed similarly to what is shown in FIG. 6, i.e. the position of the outwardly protruding collar 72 on the support member 70 and of the inwardly protruding collar 86 on the fastening member 72 can be changed around. In this case, the first fluid line 20 and the second fluid line 30 would be fluidically connected to each other when the lever is not actuated, and they could be separated from each other by actuation of the lever 90.

Figure 8:
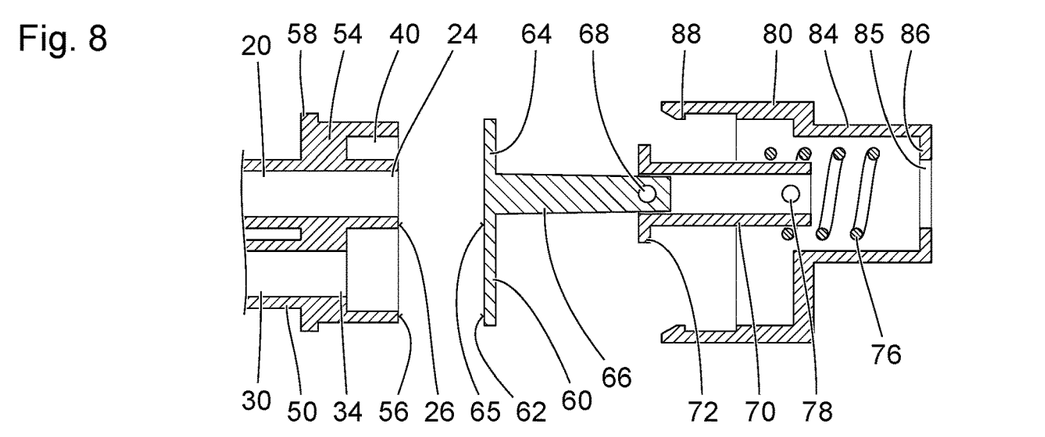
FIG. 8 shows a further schematic and enlarged view of the parts from FIG. 7.

FIG. 8 shows a further schematic sectional view of the members 50, 60, 70, 76, 80 shown in FIG. 7. The nature of the view in FIG. 8 corresponds to that of FIG. 5.

By means of the fluid line member 50 and the deformable member 60 being shown spaced apart in the view in FIG. 8, it is possible to clearly distinguish between the annular sealing surface 56 at the end face of the cylindrical wall region 57 and the corresponding annular sealing surface 62 at or near the outer edge of the flexibly movable wall region 64.

What is claimed is:

1. A medical instrument, comprising:
   a first fluid line having an end with an edge;
   a second fluid line;
   a cavity in which the end of the first fluid line is arranged, and which is connected to the second fluid line;
   wherein a wall region of the cavity is designed to be flexibly movable;
   wherein the flexibly movable wall region defines a sealing surface;
   wherein, in a first configuration, the sealing surface of the flexibly movable wall region bears on the edge of the end of the first fluid line and thus closes the end of the first fluid line; and
   wherein, in a second configuration, the sealing surface of the flexibly movable wall region does not bear, or bears only partially, on the edge of the end of the first fluid line, such that the first fluid line and the second fluid line are fluidically connected;
   wherein the sealing surface of the flexibly movable wall region is planar in the first configuration and is curved away from an open end of the first fluid line in the second configuration; and
   wherein the medical instrument further comprises a structure for lifting the flexibly movable wall region of the cavity and a spring or elastic structure surrounding a portion of the structure for lifting the flexibly movable wall region, wherein the structure for lifting the flexible movable wall region is configured to move the sealing surface into one of the first configuration or the second configuration, and a restoring force of the spring or elastic structure is configured to move the sealing surface into the other of the first configuration or the second configuration.

2. The medical instrument according to claim 1, wherein the spring or elastic structure presses the flexibly movable wall region of the cavity such that the sealing surface of the flexibly movable wall region bears against the edge of the end of the first fluid line in the first configuration.

3. The medical instrument according to claim 1, wherein the structure for lifting the flexibly movable wall region includes an extension piece and a force-transmitting structure, which is mechanically coupled to the extension piece.

4. The medical instrument according to claim 3, wherein the extension piece is integrally formed on a side of the flexibly movable wall region directed away from the cavity.

5. The medical instrument according to claim 4, wherein the structure for lifting further includes a support member, which at least partially encloses the extension piece or forms the extension piece.

6. The medical instrument according to claim 3, wherein the structure for lifting further includes a support member, which at least partially encloses the extension piece or forms the extension piece.

7. The medical instrument according to claim 3, wherein the structure for lifting the flexibly movable wall region includes a lever or a slide or a button or another manually actuatable member which is arranged at or near a proximal end of a grip member of the medical instrument, the cavity is arranged at or near a distal end of the grip member, the force-transmitting structure mechanically couples the lever or the slide or the button or the another manually actuatable member to the flexibly movable wall region.

8. The medical instrument according to claim 1, further comprising:
   wherein the structure for lifting the flexibly movable wall region includes an extension piece and a force-transmitting structure, which is mechanically coupled to the extension piece;
   wherein the structure for lifting further includes a support member, which at least partially encloses the extension piece or forms the extension piece; and
   wherein the spring or elastic structure engages on the support member, the force-transmitting structure further engages in a bore or another opening or another concave region in the support member or is in some other way mechanically coupled directly to the support member.

9. The medical instrument according to claim 1, further comprising:
   a fluid line member which includes a proximal end of the first fluid line and an end of the second fluid line; and
   a fastening member by which an annularly closed sealing surface of the flexibly movable wall region, or of a deformable member of which the flexibly movable wall region is a constituent part, is pressed against an annularly closed sealing surface of the fluid line member.

10. The medical instrument according to claim 9, wherein the flexibly movable wall region is a constituent part of the deformable member, which is cup-shaped.

11. The medical instrument according to claim 10, wherein the fastening member is cup-shaped, an annular edge region of the fastening member presses an annular sealing surface of the cup-shaped deformable member radially against the annularly closed sealing surface of the fluid line member.

12. The medical instrument according to claim 9,
wherein the structure for lifting the flexibly movable wall region includes an extension piece and a force-transmitting structure, which is mechanically coupled to the extension piece; and
wherein the fastening member includes an opening in which the extension piece is arranged, or through which the force-transmitting structure engages.

13. The medical instrument according to claim 12, wherein the structure for lifting further includes a support member, which at least partially encloses the extension piece or forms the extension piece; and
wherein the fastening member includes a tubular portion which surrounds the opening and guides the extension piece or the support member with minimal play and minimal friction.

14. The medical instrument according to claim 9, wherein the fluid line member and the fastening member are connected to each other by means of a latch connection or by another form-fit engagement.

15. The medical instrument according to claim 1, wherein the medical instrument is an endoscope with a shaft, the first fluid line or the second fluid line is arranged in the shaft.

16. The medical instrument according to claim 1, wherein the structure for lifting the flexibly movable wall region includes a force-transmitting structure coupled to the flexibly movable wall region.

17. The medical instrument according to claim 16, wherein the force-transmitting structure is indirectly coupled to the flexibly movable wall region.

\* \* \* \* \*